(12) United States Patent
Masson

(10) Patent No.: US 8,882,846 B1
(45) Date of Patent: Nov. 11, 2014

(54) SURGICAL PROCESS FOR AFFIXING AN ELBOW IMPLANT INTO THE ULNA

(71) Applicant: Marcos V. Masson, Houston, TX (US)

(72) Inventor: Marcos V. Masson, Houston, TX (US)

( * ) Notice: Subject to any disclaimer, the term of this patent is extended or adjusted under 35 U.S.C. 154(b) by 14 days.

(21) Appl. No.: 13/666,058

(22) Filed: Nov. 1, 2012

(51) Int. Cl.
| A61F 2/38 | (2006.01) |
| A61F 2/28 | (2006.01) |
| A61B 17/56 | (2006.01) |
| A61B 17/58 | (2006.01) |
| A61F 2/30 | (2006.01) |
| A61B 17/04 | (2006.01) |
| A61B 17/84 | (2006.01) |
| A61F 2/08 | (2006.01) |

(52) U.S. Cl.
CPC .................................... *A61F 2/3804* (2013.01)
USPC ......... 623/20.11; 623/16.11; 606/62; 606/64; 606/300

(58) Field of Classification Search
USPC ........... 623/20.11, 20.12, 20.13, 908; 606/62, 606/64, 102, 300
See application file for complete search history.

(56) References Cited

U.S. PATENT DOCUMENTS

| 4,131,956 A * | 1/1979 | Treace ........................ 623/20.11 |
| 4,242,758 A | 1/1981 | Amis et al. |
| 4,280,231 A | 7/1981 | Swanson |
| 4,293,963 A | 10/1981 | Gold et al. |
| 4,790,302 A * | 12/1988 | Colwill et al. .................. 606/62 |
| 4,927,422 A | 5/1990 | Engelhardt |
| 5,211,647 A * | 5/1993 | Schmieding .................. 606/104 |
| 6,217,616 B1 | 4/2001 | Ogilvie |
| 6,302,915 B1 * | 10/2001 | Cooney et al. ............. 623/21.12 |
| 7,419,507 B2 * | 9/2008 | Cook et al. .................. 623/20.13 |
| 2007/0276382 A1 * | 11/2007 | Mikhail et al. .................. 606/62 |
| 2011/0172781 A1 | 7/2011 | Katrana et al. |

OTHER PUBLICATIONS

Olecranon Osteotomy Nail Technique Guide. Synthes. Copyright 2009.*

* cited by examiner

*Primary Examiner* — Thomas J Sweet
*Assistant Examiner* — Christie Bahena
(74) *Attorney, Agent, or Firm* — Egbert Law Offices, PLLC

(57) ABSTRACT

A surgical process for affixing an elbow implant into the ulna has the steps of separating the olecranon process from the ulna so as to expose an end of an intermedullary canal of the ulna, inserting a stem of the elbow implanted into the intermedullary canal such that an end of the stem extends outwardly of the end of the ulna, and affixing the olecranon process onto the exposed end of the ulna. A hole is drilled through the olecranon process such that the hole is axially aligned with the intermedullary canal of the ulna. This hole is drilled prior to the step of separating.

16 Claims, 3 Drawing Sheets

SURGICAL PROCESS FOR AFFIXING AN ELBOW IMPLANT INTO THE ULNA

CROSS-REFERENCE TO RELATED APPLICATIONS

Not applicable.

STATEMENT REGARDING FEDERALLY SPONSORED RESEARCH OR DEVELOPMENT

Not applicable.

NAMES OF THE PARTIES TO A JOINT RESEARCH AGREEMENT

Not applicable.

INCORPORATION-BY-REFERENCE OF MATERIALS SUBMITTED ON A COMPACT DISC

Not applicable.

BACKGROUND OF THE INVENTION

1. Field of the Invention

The present invention relates to surgical processes for attaching prosthesis and implants onto the humerus and ulna of a human arm. More particularly, the present invention the relates to surgical procedures for affixing an elbow implant whereby the olecranon process is removed from the ulna prior to the installation of the elbow implant. Additionally, the present invention relates to surgical processes whereby the elbow implants are installed within the ulna without the use of cement.

2. Description of Related Art Including Information Disclosed Under 37 CFR 1.97 and 37 CFR 1.98

The bones of the human skeleton are joined by a variety of different bone joints. Joints may be classified into two main structural types, namely diarthroses and synarthroses. Diarthroses are joints having a joint cavity between the articulating surfaces of the bones. Synarthroses are joints which have tissues growing between their articulating surfaces. The tissue does not permit free movement between the articulating surfaces.

Diarthrotic joints besides having a joint cavity include a thin layer of hyaline cartilage covering the joint surfaces of the articulating bones. A sleeve-like, fibrous capsule lined with a smooth, slippery synovial membrane encases the joint. Ligaments grow between the bones to constrain and latch the bones firmly together. Diarthrotic joints permit one or more of a variety of movements including flexion, extension, abduction, adduction, rotation, circumduction and special movements such as supination, pronation, inversion, eversion, protraction and retraction.

The broad joint classification may be broken down into subtypes based upon the structural relationship of the bones at the joints and the movements involved. These subtypes include the ball-and-socket joint, the hinge or ginglymous joint, the pivot or trochoid joint, the condyloid joint, the saddle joint and the gliding or arthrodial joint.

Procedures have been developed for repairing severely diseased or damaged joints when significant stiffness, pain or loss of motion is present. These procedures have included arthroplasty, that is, removal of the defective bone portions and partial implant replacement, which essentially involves resurfacing of one of the articulating bone surfaces with a prosthesis. Total joint prostheses have been developed which entirely replace the joint. Such prosthetic devices have been employed for replacement of finger joints, knee joints and elbow joints, for example.

The elbow is a diarthrotic joint formed by articulation of the distal humerus with both the radius and the ulna. Stability depends on the shape of the joint articular surfaces and the maintenance of their coaptation by the ligaments and muscles surrounding the joint. A hinge joint exits at the ulnar humeral articulation allowing movement of flexion and extension only. The articulation between the radius and the humerus is a trochoid or pivot joint which allows nearly all movements of pronation and supination of the forearm. The distal humerus includes the trochlea which articulates with the semilunar notch of the ulna and the capitulum which articulates with the proximal surface of the radial head. The vertical margin of the radial head rotates with the radial notch of the ulna.

Repair of diseased or damaged elbow joints has included resection arthroplasty, implant replacement of the radial head, flexible implant resection arthroplasty of the elbow joint and the use of rigid metal hinge devices for arthroplasty of the elbow joint. Reconstitution with prior hinge type total prostheses has presented various problems relating to stability of the joint, loosening of the implant, excessive bone stock removal and transmission of excessive stress to the bones by the implant.

There are two main design types of elbow prosthetic systems. These include linked systems and unlinked systems. The linked implants ensure joint stability. This stability allows a more aggressive soft tissue release in the presence of stiffness and deformity. The linked implants are used in the setting of significant bone loss or ligamentous insufficiency. On the other hand, the increased constraint results in increased tension across the joint surface, possibly leading to component loosening (most commonly humeral) or polyethylene failure.

Unlinked components are less constrained and thus may be associated with less mechanical failure. The shorter stems in unlinked components may be beneficial in revision surgery. In addition, some unlinked humeral components can be used as hemiarthropasties. However, dislocation is possible with unlinked components. Adequate humeral condyles are required for unlinked implants, along with appropriate soft tissue support, and this could limit the amount of soft tissue release for stiffness or contractures.

The Zinmmer Coonrad-Morrey™ total elbow system is a semi-constrained hinged prosthesis with a high molecular-weight polyethylene bushing. Current designs have a seven degree rotary toggle. Twelve humeral and ulnar stems allow comprehensive patient matching with intraoperative flexibility. Both of the components are fixed with polymethyl methacrylate and fixed with axis pins which articulate with the polyethylene bushings. The humeral stem is triangular in shape to maximize stability by minimizing rotation. The anterior humeral flange permits insertion of bone graphs anteriorly to enhance thickening of bone stock where maximum stress occurs, reducing posterior displacement and torsional forces, and helping to protect the bone-cement-implant surface. The ulnar stem is quadangular in shape to minimize intermedullary rotation.

The Biomet Discover™ elbow system is linked prosthesis that features spherical condyles on the hinge to allow increased articular surface contact. Hinge laxity permits proper anatomic varus/valgus movement in the elbow, and the spherical condyles can be assembled in the joint via posterior approach. In addition, a cylindrical base preserves bone to minimize stress risers at the supracondylar columns. Seven degrees of varus/valgus laxity is comparable to that of the Zimmer prosthesis, along with the anterior flange for enhanced rotation stability.

In the systems of prosthetic elbow replacement, it is necessary to form a large diameter hole through the olecranon process so as to provide an opening whereby the stem of the stem of the prosthetic implant can be inserted. In order to form the proper hole, it is necessary to sever the triceps tendon which covers the posterior portion of the olecranon process. The formation of the large diameter opening must align with the intermedullary canal of the ulna. After the installation and cementing of the stem of the prosthesis into the intermedullary canal, the triceps tendon is then sutured back together at the posterior of the olecranon process. The suturing process is rather complicated and time-consuming. Additionally, it requires a great deal of time for the triceps tendon to effectively heal following the surgical procedure. As such, a need has developed to provide a surgical process whereby the triceps tendon is not severed during the surgical procedure.

In prior elbow implants, the stem of the elbow implant is cemented into to position within the intermedullary canal. In certain circumstances, the cement is improperly applied to the stem such that the stem is not secure within the intermedullary canal. In other circumstance, the heat of the cement can burn bone such that the healing processes will not effectively secure the stem to the bone. As such, a need has developed so as to be able to install the stem of the elbow implant without the use of cement.

In the past, various patents have issued relating with respect to elbow implants and the surgical procedures that are use to install such elbow implants. For example, U.S. Pat. No. 4,131,956, issued on Jan. 2, 1979 to J. T. Treace, is an early patent for an elbow prosthesis for replacing one or more of the articulating surfaces of the elbow joint in a human elbow. An ulna component is fixedly anchored to the proximal end of the ulna. The ulna component is provided with a head member having a curved face portion for replacing the articulating surface of the proximal end of the ulna. A humeral component is fixedly anchored to the distal end of the humerus and is provided with a head member having a curved face portion for replacing the articulating surface of the distal end of the humerus.

U.S. Pat. No. 4,242,758, issued on Jan. 6, 1981 to Amis et al., shows an elbow prosthesis having a humeral component with spherical, articular surface portions which together extend over substantially the entire length of the component and are shaped and dimensioned for improving fit with the ulna and radius or with prosthetic components located thereon.

U.S. Pat. No. 4,280,231, issued on Jul. 28, 1981 to A. B. Swanson, provides an elbow prosthesis which has a humeral component having a body portion defining a plurality of generally semi-circular distal bearing surfaces extending therefrom and a proximally extending intermedullary canal stem. An ulnar component has a body portion defining a convex posterior surface adapted to be received within a prepared semi-lunar notch of the ulna, a plurality of semi-circular grooves configured to matingly receive the distal bearing surfaces of the humeral component, and a distally extending intermedullary canal stem. The ulnar component further defines a laterally positioned capitulum process having a distal surface adapted to be abutted against by the head of the radius bone upon implantation. The humeral component defines an aperture and the ulnar component includes a hook-like member adapted to detachably and hingingly interconnect the components in a slipfit fashion.

U.S. Pat. No. 4,293,963, issued on Oct. 13, 1981 to Gold et al., teaches an unrestrained elbow prosthesis that includes a humeral implant component and an ulnar implant component. The humeral component has an elongated stem with a substantially cylindrical articulating surface on the distal end of said stem wherein the cylindrical articulating surface is convex such that the diameters of the end surfaces of the cylindrical shape are smaller than the diameter about the midportion of the cylindrical shape. The ulnar component is comprised of a metal retainer and a polyethylene bearing. The metal retainer includes an elongated stem attached to a metal base such that the stem depends from the base and anatomically curves slightly outward or laterally from the base. The polyethylene bearing is slidably engaged to the metal retainer and locks into position on the retainer. The metal humeral component then rotates about the axis of its cylindrical articulating surface within the cavity of the ulnar bearing.

U.S. Pat. No. 4,927,422 issued on May 22, 1990 to J. A. Engelhardt, shows elbow arthroplasty instrumentation and surgical procedure. This arthroplasty procedure is for modifying the distal end of the humerus deformed by injury or disease in preparation for fixation of an elbow joint replacement. A through hole is first formed in the superior aspect of the olecranon fossa communicating with the humeral canal. A stem member which extends from the platform of a distal cut guide tool is received through the hole and extends into the humeral canal. The distal cut guide tool is held so that the platform is generally coplanar with the junction of the medial epicondyle and the trochlea with proper inclinations, both in an anterior view and in a lateral view. Thereupon, a first resected surface is formed by sawing, using as a guide, a planar guiding surface provided on the platform. With removal of the distal cut guide tool, a broach and chamfer cut guide tool having a plurality of saw guide slots is positioned on the first resected surface and additional cuts are made with the aid of the latter tool to form a wedge of bone onto which a humeral prosthesis can be impacted.

U.S. Pat. No. 6,217,616, issued on Apr. 17, 2001 to W. F. Ogilvie, provides an asymmetric and axisymmetric prostheses for replacement of the radial head of an elbow so as to smoothly interengage with the annular ligament of the radius so as to effectively allow a patient to recover normal functioning of the forearm. These prostheses have head, collar and stem sections. The undersurface of the head which surrounds the collar provides a shoulder which is gripped by the annular ligament through which the prosthesis is inserted during implantation.

U.S. Patent Publication No. 2011/0172781, published on Jul. 14, 2011 to Katrana et al., provides an elbow prosthesis that can include a capitellar implant that has an articulating head and a stem. The articulating head can have a first substantially hemispherical portion and a second portion that collectively extends between lateral and medial sides of the articulating head and are separated by a plane. The first and second portions can extend between the lateral and medial sides. The second portion can generally have an attachment lobe that extends on the lateral side and that defines a passage therethrough. The passage can extend at least partially on the second side.

It is an object of the present invention to provide a surgical process that effectively secures the stem of an elbow implant within the intermedullary canal of the ulna.

It is another object of the present invention to provide a surgical process which greatly improves visibility during the surgical process.

It is another object of the present invention to provide a surgical process for installing an elbow implant which eliminates the need to cut the triceps tendon and the suturing of the triceps tendon.

It is a further object of the present invention to provide a surgical process for affixing an elbow implant which avoids the use of cement.

It is another object of the present invention to provide a surgical process for affixing an elbow implant that eliminates micromotion of the implant within the intermedullary canal of the ulna.

It is a further object of the present invention to provide a surgical process for affixing an elbow implant which allows the elbow implant to be rapidly installed.

It is still a further object of the present invention to provide a surgical process which improves healing ability, reduces infection and minimizes operating time.

These and other objects and advantages of the present invention will become apparent from a reading of the attached specification and appended claims.

BRIEF SUMMARY OF THE INVENTION

The present invention is a surgical process for affixing an elbow implant into the ulna that includes the steps of: (1) separating the olecranon process from the ulna so as to expose an end of an intermedullary canal of the ulna; (2) inserting a stem of the elbow implant into the intermedullary canal such that an end of the stem extends outwardly of the end of the ulna; and (3) affixing the olecranon process onto the exposed end of the ulna.

In the process of the present invention, a small hole is drilled through the olecranon process such that the hole is generally aligned with the longitudinal axis of the intermedullary canal of the ulna. This step of drilling occurs prior to the step of separating. The intermedullary canal is reamed by inserting a reaming tool into the intermedullary canal at the exposed end of the ulna.

The present invention utilizes a unique arrangement whereby the stem of the elbow implant can be fixed to the ulna. In particular, a jig is applied onto the exposed end of the ulna. A slot of the jig is aligned adjacent with a surface of the ulna away from the exposed end of the ulna. A cross hole is formed through the surface of the ulna by drilling through the slot of the jig. The stem of the elbow implant is affixed within the intermedullary canal by securing a screw through the cross hole and into the stem of the elbow implant. The jig has a trial stem and a head at an end of the trial stem. The trial stem has a cross-hole formed therethrough. A bracket is attached to the head of the head of the trial stem. The bracket has a surface extending adjacent to the surface of the ulna. The surface of the bracket has the slot formed therethrough. The slot is aligned with the cross-hole of the trial stem. The jig is removed from the ulna following the step of drilling.

The elbow implant has a screw hole formed therein. The step of affixing the olecranon process includes inserting a screw into the screw hole so as to affix the olecranon process onto the exposed end of the ulna. The screw is a cannulated screw having an external thread and an internal thread. The screw is screwed into the screw hole of the elbow implant such that the external thread of the cannulated screw engages an internal thread of the screw hole of the elbow implant and such that the external thread engages with a wall of the drilled hole of the olecranon process. Another screw is screwed into the cannulated screw such that an external thread of the another screw is threadedly secured to the internal thread of the cannulated screw. This another screw has a surface bearing against the surface of the olecranon process. This another screw has a head at an end thereof. This head bears against the surface of the olecranon process such that the olecranon process is in surface-to-surface contact with the exposed end of the ulna.

DETAILED DESCRIPTION OF THE INVENTION

Figure 1:
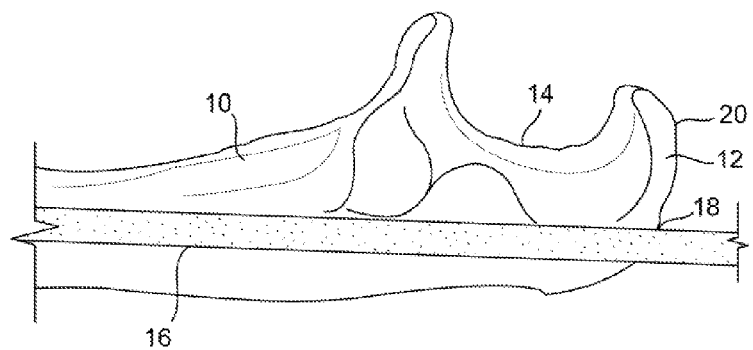
FIG. 1 is a side elevational view showing the formation of a small hole through the olecranon process and ulnar according to the first step of the procedure of the present invention.

Referring to FIG. 1, there is shown the ulna 10 having an olecranon process 12 at an end thereof. The greater sigmoid notch 14 is formed in the area between the ulna 10 and the olecranon process 12. The ulna 10 has an intermedullary canal 16 extending longitudinally therethrough.

As can be seen in FIG. 1, in the initial step of the process of the present invention, a small hole 18 is drilled through the olecranon process at the end thereof. This hole 18 will be drilled so as to be in generally axial alignment with the intermedullary canal 16. Unlike the prior art, the hole 18 that is drilled in an area below the surface 20 where the triceps tendon is attached. As such, the relatively small hole 18 can be formed. In this arrangement, the olecranon process 12 is pre-drilled prior to the remaining steps of the process of the present invention.

Figure 2:
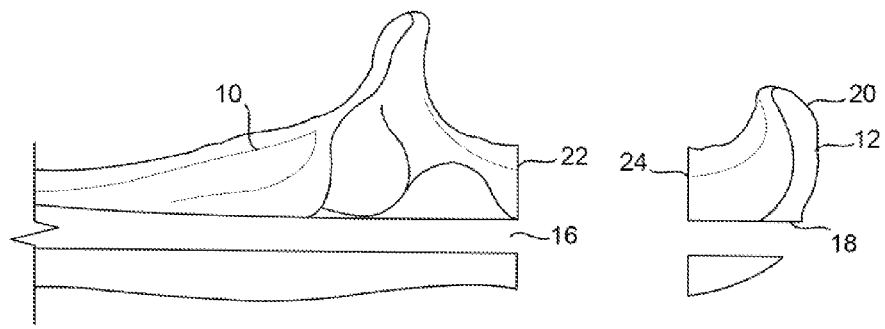
FIG. 2 is side elevational view showing the olecranon process as separated from the ulna so as to leave an exposed end of the ulna.

In FIG. 2, it can be seen that the hole 18 has been formed in the olecranon process 12. The olecranon process is sawed so as to be separated from the ulna 10. As such, the ulna 10 will have an exposed end 22 at an end thereof. The olecranon process 12 will have a surface 24 that is complementary to and matable with the exposed end 22 of the ulna 10. The intermedullary canal 16 will open at the exposed end 22 of the ulna 10. In FIG. 2, the triceps tendon will continue to be attached to the surface 20 of the olecranon process 12. As a result, it is not necessary to sever or cut the triceps tendon during the process of the present invention.

Figure 3:
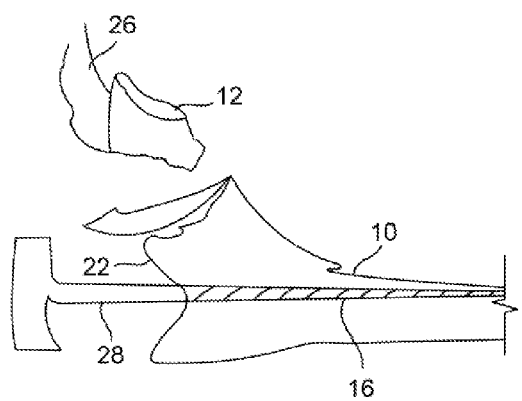
FIG. 3 is a side transparent view showing the reaming of the intermedullary canal of the ulna.

In FIG. 3, the olecranon process 12 has been removed from the exposed end 22 of the ulna 10. The triceps tendon 26 continues to remain attached to the olecranon process 12. The olecranon process 12 and the triceps tendon 26 can be moved away from the exposed end 22 of the ulna 10.

So as to allow for the intermedullary canal 16 to properly receive the stem of the elbow implant, a reaming tool 28 is inserted into the intermedullary canal 16. The reaming tool 28 is a manual reaming tool 28 that can be suitably rotated so as to create a smooth surface on the wall of the intermedullary canal 16.

Figure 4:
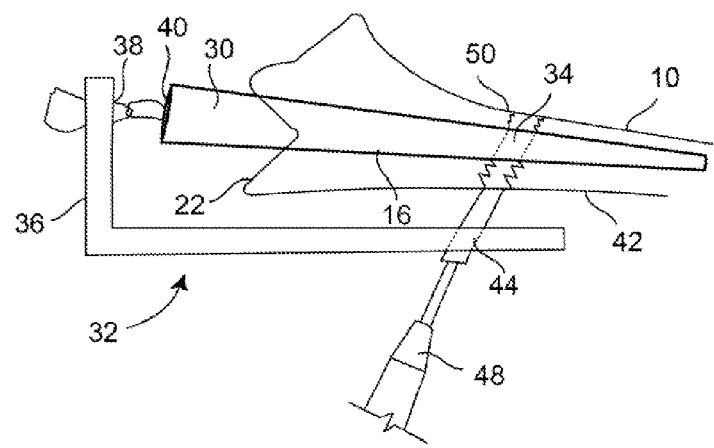
FIG. 4 is a side elevational view showing the use of a jig for the formation of a cross hole in the ulna.

In FIG. 4, the reaming tool 28 has been removed from the intermedullary canal 16. A trial stem 30 of a jig 32 is inserted into the intermedullary canal. The trial stem 30 will have a size suitable for proper fitting within the intermedullary canal 16. As such, it will have a configuration reflecting the configuration of the stem of the elbow implant. The trial stem 30 has a cross hole 34 formed therethrough.

A bracket 36 can be affixed to a head 38 at the end 40 of the trial stem 30. The end 40 extends outwardly of the exposed end 22 of the ulna 10. The head 38 properly receives the bracket 36 such that the bracket 36 will be aligned generally adjacent to the outer surface 42 of the ulna 10. The bracket 36 is an L-shaped bracket that is securely affixed to the head 38. The bracket 36 will have a guide hole 44 formed therethrough. Guide hole 44 will be axially aligned with the cross hole 34 of the trial stem 30. The guide hole 44 can be in the nature of a slot that is formed through the portion of the bracket 36 that is aligned with the exterior surface 42 of the ulna 10.

A suitable drill 48 can be inserted through the guide hole 44. Since the guide hole 44 is aligned with the cross hole 34 of the trial stem 30, the drill 48 can properly drill a hole through the ulna 10 that is in alignment with the cross hole 34.

After the drilling operation is complete, the drill 48 can be removed from the guide hole 44 and from the interior of the ulna 10. The remaining cross hole 50 will extend diametrically through the ulna 10. After the hole is formed, the trial stem 30, along with the associated jig 32 can be removed. As a result, the ulna 10 will have the cross hole 50 formed in a proper location for the receipt of the stem of the elbow implant therein.

Figure 5:
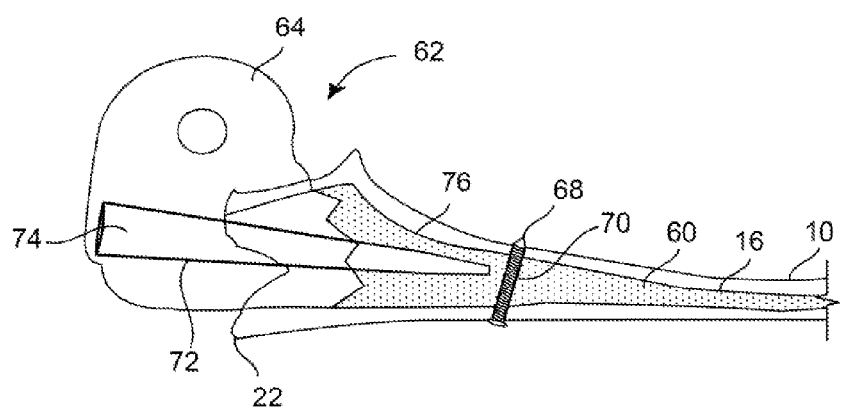
FIG. 5 is an illustration of a further step in the process of the present invention in which a cannulated screw is inserted into the end of the stem of the implant.

As can be seen in FIG. 5, the stem 60 of the elbow implant 62 is received within the intermedullary canal 16 of the ulna 10. The stem 60 will have a spool 64 formed at the end thereof outwardly of the exposed end 22 of the ulna 10. A screw 68 will extend through the ulna 10 and through a cross hole 70 formed in the stem 60 of the elbow implant 62. As such, the screw 68 will engage with the bone of the ulna 10 and through the cross hole 70 of the stem 60 so as to securely fix the stem 60 within the intermedullary canal 16 without the use of cement. As a result, the stem 60 is securely fixed in position within the intermedullary canal 16.

The elbow implant 62 will have a hole 72 extending thereinto. A cannulated screw 74 will have an external thread on an outside thereof and an internal thread. The external thread will be received within a threaded section 76 formed at the end of the stem 60 and through the spool 64. The cannulated screw 74 will extend outwardly of the exposed end 22 of the ulna 10.

Figure 6:
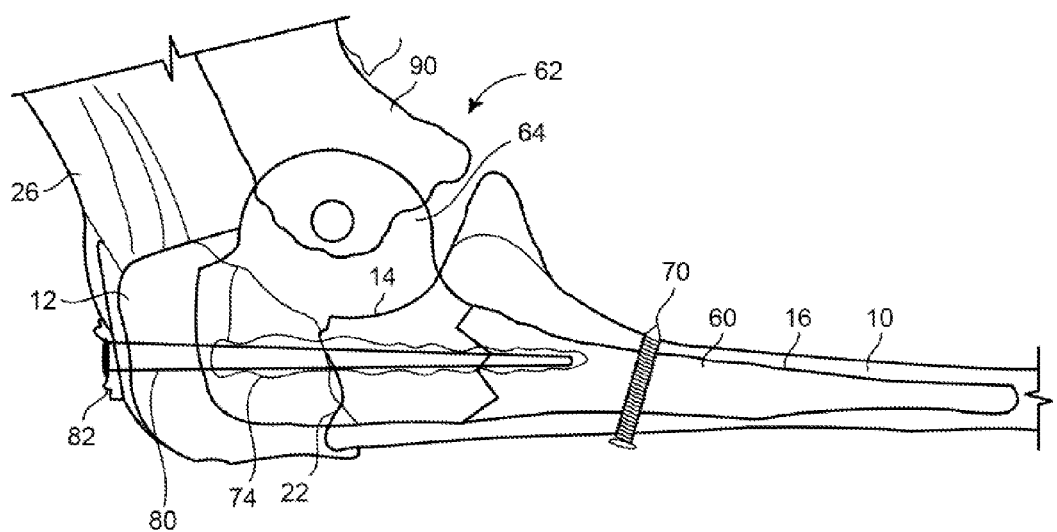
FIG. 6 is a side elevational view showing the olecranon process as secured by another screw within the cannulated screw of the implant.

In FIG. 6, it can be seen that the stem 60 is affixed within the intermedullary canal 16 of the ulna 10. The screw 70 affixes the stem 60 in a proper position. Another screw 80 will have external threads that engage with the internal threads of the cannulated screw 74. A wide diameter head 82 is formed at the end of the another screw 80. As a result, the olecranon process 12 can be moved in position onto the exposed end 22 of the ulna 10 so as to be in surface-to-surface contact with the exposed end 22. The another screw 80 is inserted so as to engage with the internal threads of the cannulated screw 74. The head 82 will bear against the exterior surface of the olecranon process 12 so as to fix the olecranon process 12 into surface-to-surface contact with the exposed end 22 of the ulna 10. The triceps tendon 26 will continue to extend from the olecranon process 12.

The spool 64 of the elbow implant 62 extend outwardly of the sigmoid notch 14. Another portion 90 of the elbow implant 62 will be hingedly connected to the spool 64 in a conventional manner.

Figure 7:
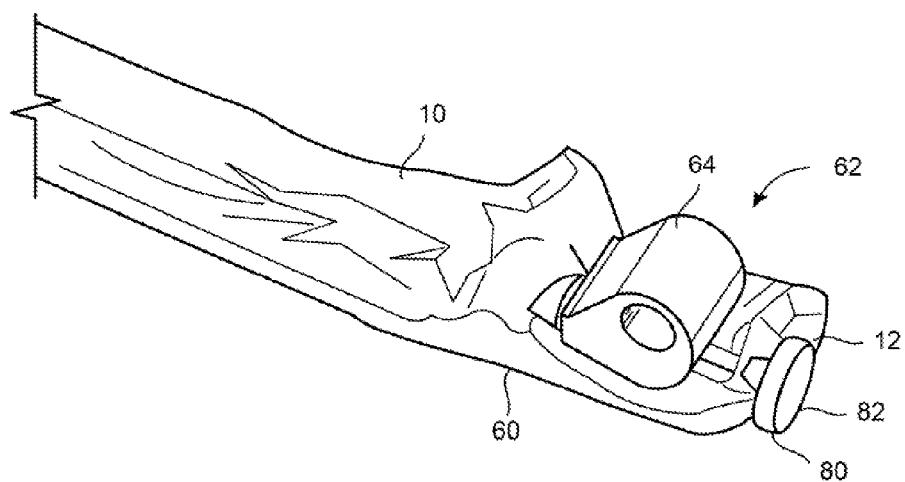
FIG. 7 is perspective view showing the implant as received within the ulna.

FIG. 7 illustrates the manner in which the elbow implant 62 is affixed within the ulna 10. In FIG. 7, it can be seen that the stem 60 of the elbow implant 62 is received within the intermedullary canal 16 of the ulna 10. The spool 64 will extend upwardly and outwardly of the exposed end 22 of the ulna 10. The another screw 80 is threadedly secured within the elbow implant 62. The head 82 will bear against the outer surface of the olecranon process 12. As such, the tightening of the another screw 80 will draw the olecranon process 12 into surface-to-surface contact with the exposed end 22 of the ulna 10. As a result, the elbow implant 62 is properly installed within the ulna 10 in a convenient manner.

In particular, the present invention achieves significant advantages over the prior art. In particular, in the surgical process of the present invention, the problems associated with the lack of visibility caused by the olecranon process 12 are effectively avoided. In order to gain access to the intermedullary canal 16 of the ulna 10, the olecranon process 12 is sawed so as to separate therefrom. The olecranon process 12 can then be moved into a position away from the exposed intermedullary canal at the exposed end of the ulna 10. As a result, it is relatively easy to ream the intermedullary canal of the ulna 10. Additionally, this access allows the stem of the elbow implant 62 to be easily inserted within the intermedullary canal. The jig 32 associated with the present invention assures that a properly alignment can be achieved with the cross hole of the stem of the elbow implant 12 such that the stem of the elbow implant 12 can be affixed within the ulna 10 through the use of screws. As a result, the cementing processes of the prior art are effectively avoided.

Since only a small hole is initially drilled in the olecranon process 12, there is no need to sever the triceps tendon from the olecranon process. Additionally, the present invention avoids the problems associated with the drilling of a relatively large hole through the olecranon process. Since the olecranon process 12 is positioned onto the exposed end 22 of the ulna 10 following the installation of the elbow implant 62, the bone can heal naturally. There is no need to suture the tendon. As such, the triceps tendon will remain undamaged during the installation of the elbow implant 62. The use of the cannulated screw facilitates the ability to establish a strong and secure connection between the olecranon process 12 and the ulna 10. Additionally, and furthermore, the process of the present invention allows a proper angular relationship between the portion of the elbow implant 62 to achieved. The use of the jig assures a proper alignment between the portions of the elbow implant 62.

In the process of the present invention, the installation of the elbow implant can be achieved in a very safe, efficient and convenient manner. Great precision associated with the formation of holes for the placement of elbow implant is not necessary. The easy access to the intermedullary canal assures that the procedure is easily carried out. As a result, surgical time is minimized. The reduced surgical time serves to further reduce the possibility of infection during the surgical procedure. Additionally, the healing time required is also significantly reduced.

The foregoing disclosure and description of the invention is illustrative and explanatory thereof. Various changes in the details of the described method can be made within the scope of the present invention without departing from the true spirit of the invention. The present invention should only be limited by the following claims and their legal equivalents.

I claim:

1. A surgical process for affixing an elbow implant into the ulna, the surgical process comprising: drilling a hole through an olecranon process such that said hole is generally axially aligned with an intermedullary canal of the ulna: subsequently separating art the olecranon process with a triceps tendon attached thereto from the ulna so as to expose an end of an intermedullary canal of the ulna; inserting a stem of the elbow implant into the intermedullary canal, said stem having an end extending outwardly of the end of the ulna, the step of inserting the stem being subsequent to the step of separating the olecranon process; and affixing said olecranon process with the triceps tendon attached thereto onto the exposed end of the ulna; wherein the elbow implant has a body with a hinged relationship extending transverse to the stem and a screw hole formed axially along the stem, the step of affixing said olecranon process comprising: inserting a screw into said screw hole so as to affix said olecranon process onto the exposed end of the ulna.

2. The surgical process of claim 1, further comprising:
reaming the intermedullary canal by inserting a reaming tool into the intermedullary canal at the exposed end of the ulna.

3. The surgical process of claim 1, further comprising:
applying a jig onto the exposed end of the ulna, said jig having a slot formed therein;
aligning said slot of said jig adjacent to a surface of the ulna away from the exposed end; and
drilling through said slot of said jig so as to form a cross hole through the surface of the ulna.

4. The surgical process of claim 3, further comprising:
affixing said stem of said elbow implant within said intermedullary canal of the ulna by securing a screw through said cross hole and into said stem of said elbow implant.

5. The surgical process of claim 3, said jig having a trial stem and a head at an end of said trial stem, said trial stem having a cross-hole formed therethrough, the step of applying the jig comprising:
attaching a bracket onto said head of said trial stem, said bracket having a surface extending adjacent to the surface of the ulna, said surface of said bracket having said slot formed therethrough, said slot being aligned with said cross-hole of said trial stem.

6. The surgical process of claim 3, further comprising:
removing said jig from said ulna following the step of drilling.

7. The surgical process of claim 3, said screw being a cannulated screw having an external thread and an internal thread, the step of inserting the screw comprising: screwing said screw into said screw hole of the elbow implant such that said external thread of said cannulated screw engages an internal thread of said screw hole of the elbow implant and such that the external thread engages with a wall of the drilled hole of the olecranon process.

8. The surgical process of claim 7, the step of inserting the screw further comprising:
screwing another screw into said cannulated screw such that an external thread of said another screw is threadedly secured to said internal thread of said cannulated screw, said another screw having a surface bearing against a surface of the olecranon process.

9. The surgical process of claim 8, said another screw having a head at an end thereof, the step of screwing comprising:
bearing said head of said another screw against the surface of the olecranon process so that the olecranon process is in surface-to-surface contact with the exposed end of the ulna.

10. A surgical process for affixing an elbow implant into the ulna, the surgical process comprising: drilling a hole through an olecranon process with a triceps tendon attached thereto, said hole being aligned with an intermedullary canal of the ulna; subsequently separating the olecranon process from the ulna so as to expose an end of the ulna and the intermedullary canal of the ulna; affixing a stem of the elbow implant into the intermedullary canal such that said stem is non-rotatable relationship within the intermedullary canal, said stem having an end extending outwardly of the exposed end of the ulna, the step of affixing the stem being subsequent to the step of separating the olecranon process; and securing the olecranon process with the triceps tendon attached thereto back onto the exposed end of the ulna such that said olecranon process is in surface-to-surface contact with the exposed end of the ulna, the elbow implant having a portion extending in a hinged relation with said stem and extending outwardly of the olecranon process and transverse to the stem; the elbow implant having a screw hole formed axially along the stem, the step of securing comprising: inserting a screw into said screw hole so as to affix said olecranon process onto the exposed end of the ulna.

11. The surgical process of claim 10, further comprising:
applying a jig onto the exposed end of the ulna, said jig having a slot formed therein;
aligning said slot of said jig adjacent to a surface of the ulna away from the exposed end; and
drilling through said slot of said jig so as to form a cross hole through the surface of the ulna.

12. The surgical process of claim 11, further comprising:
affixing said stem of said elbow implant within said intermedullary canal of the ulna by securing a screw through said cross hole and into said stem of said elbow implant.

13. The surgical process of claim 11, said jig having a trial stem and a head at an end of said trial stem, said trial stem having a cross-hole formed therethrough, the step of applying the jig comprising:
attaching a bracket onto said head of said trial stem, said bracket having a surface extending adjacent to the surface of the ulna, said surface of said bracket having said slot formed therethrough, said slot being aligned with said cross-hole of said trial stem.

14. The surgical process of claim 10, said screw being a cannulated screw having an external thread and an internal thread, the step of inserting the screw comprising: screwing said screw into said screw hole of the elbow implant such that said external thread of said cannulated screw engages an internal thread of said screw hole of the elbow implant and such that the external thread engages with a wall of the drilled hole of the olecranon process.

15. The surgical process of claim 14, the step of inserting the screw further comprising:
screwing another screw into said cannulated screw such that an external thread of said another screw is threadedly secured to said internal thread of said cannulated screw, said another screw having a surface bearing against a surface of the olecranon process.

16. The surgical process of claim 15, said another screw having a head at an end thereof, the step of screwing comprising:

bearing said head of said another screw against the surface of the olecranon process so that the olecranon process is in surface-to-surface contact with the exposed end of the ulna.

\* \* \* \* \*